(12) United States Patent
Santi et al.

(10) Patent No.: US 6,838,265 B2
(45) Date of Patent: Jan. 4, 2005

(54) OVERPRODUCTION HOSTS FOR BIOSYNTHESIS OF POLYKETIDES

(75) Inventors: Daniel Santi, San Francisco, CA (US); Robert McDaniel, Palo Alto, CA (US); Li Tang, Foster City, CA (US); Chaitan Khosla, Palo Alto, CA (US)

(73) Assignee: Kosan Biosciences, Inc., Hayward, CA (US)

(*) Notice: Subject to any disclaimer, the term of this patent is extended or adjusted under 35 U.S.C. 154(b) by 0 days.

(21) Appl. No.: 09/847,526

(22) Filed: May 1, 2001

(65) Prior Publication Data

US 2002/0004229 A1 Jan. 10, 2002

Related U.S. Application Data

(60) Provisional application No. 60/201,287, filed on May 2, 2000.

(51) Int. Cl.⁷ .................................................. C12P 19/62
(52) U.S. Cl. ........................................................ 435/76
(58) Field of Search ................................ 435/76, 252.3, 435/254.11, 254.21

(56) References Cited

U.S. PATENT DOCUMENTS 5,672,491 A    9/1997   Khosla et al.
5,962,290 A   10/1999   Khosla et al.
6,177,262 B1   1/2001   Ziermann et al.

FOREIGN PATENT DOCUMENTS

| WO | WO 98/49315 | 11/1998 |
| WO | WO 99/61599 | 12/1999 |
| WO | WO 00/24907 |  5/2000 |
| WO | WO 00/26349 |  5/2000 |
| WO | WO 00/63361 | 10/2000 |

OTHER PUBLICATIONS

Brown et al., J. Bacteriol. (1990) 172(4):1877–1988.

Brown et al., Mol. Gen. Genet. (1994) 242:185–193.

Matsushima et al., Gene (1994) 146:39–45.

Pacey et al., J. Antibiotics (1998) 51(11):1029–1034.

Vinci and Byng, Strain Improvement by Nonrecombinant Methods, in: Manual of Industrial Microbiology and Biotechnology, Second Edition, Demain et al. (eds.), ASM Press, Washington, D.C. (1999) pp. 103–113.

*Primary Examiner*—Terry McKelvey
(74) *Attorney, Agent, or Firm*—Morrison & Foerster LLP

(57) ABSTRACT

Generic overproduction host cells can be used to produce any polyketide and obviate the need for performing conventional strain improvement.

2 Claims, 3 Drawing Sheets

SEQUENCE LISTING

<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: eryAI left flank, forward primer

<400> SEQUENCE: 1
tttgcatgcg gccacgcgca cgtcgtgacc                                    30

<210> SEQ ID NO 2
<211> LENGTH: 34
<212> TYPE: DNA
<213> ORGANISM: Artificial Sequence
<220> FEATURE:
<223> OTHER INFORMATION: eryAI left flank, reverse primer

<400> SEQUENCE: 2
ttaagcttca tatgtccccc tactcgacga ccac                               34

```
<210> SEQ ID NO 3
<211> LENGTH: 34
<212> TYPE: DNA
<213> ORGANISM: Artificial Sequence
<220> FEATURE:
<223> OTHER INFORMATION: eryAIII right flank, forward primer

<400> SEQUENCE: 3
tttggatccg gcggagggaa tacatgacca cgac                             34

<210> SEQ ID NO 4
<211> LENGTH: 30
<212> TYPE: DNA
<213> ORGANISM: Artificial Sequence
<220> FEATURE:
<223> OTHER INFORMATION: eryAIII right flank, reverse primer

<400> SEQUENCE: 4
tttgaattcc cgctcgctga agtccaggct                                  30

<210> SEQ ID NO 5
<211> LENGTH: 51
<212> TYPE: DNA
<213> ORGANISM: Artificial Sequence
<220> FEATURE:
<223> OTHER INFORMATION: annealed oligonucleotide

<400> SEQUENCE: 5
agcttcgggt gccagggcgt gcccttgggc tccccgggcg cgtaactagt g           51

<210> SEQ ID NO 6
<211> LENGTH: 51
<212> TYPE: DNA
<213> ORGANISM: Artificial Sequence
<220> FEATURE:
<223> OTHER INFORMATION: annealed oligonucleotide

<400> SEQUENCE: 6
gatccactag ttacgcgccc ggggagccca agggcacgcc ctggcacccg a           51
```

OVERPRODUCTION HOSTS FOR BIOSYNTHESIS OF POLYKETIDES

CROSS-REFERENCE TO RELATED APPLICATIONS

This application claims priority to provisional U.S. patent application Ser. No. 60/201,287, filed May 2, 2000.

STATEMENT OF RIGHTS TO INVENTIONS MADE UNDER FEDERALLY SPONSORED RESEARCH

This invention was made with United States government support in the form of a grant (R43 AI47567) from the NIH; the United States government has certain rights to this invention.

TECHNICAL FIELD

The present invention provides recombinant methods and materials for producing polyketides by recombinant DNA technology. The invention relates to the fields of agriculture, animal husbandry, chemistry, medicinal chemistry, medicine, molecular biology, pharmacology, and veterinary technology.

BACKGROUND ART

Polyketides are an important class of natural products responsible for the development of many human therapeutic, veterinary, and agricultural products (e.g. FK506, lovastatin, and avermectin). The enzymes which synthesize these compounds, polyketide synthases (PKSs), have been the target of various molecular engineering methods aimed at producing either improved analogs of existing pharmaceuticals or combinatorial libraries of novel polyketides. Modular PKSs—such as the 6-deoxyerythronolide B synthase (DEBS) shown in FIG. 1 have been altered by such techniques to produce new polyketide structures derived by genetic manipulation of one or more of the enzymatic domains contained in such PKS enzymes (see U.S. Pat. No. 5,962,290 and PCT Pub. No. 98/49315, supra).

These first-generation successes have since led to a rapid proliferation of genetically engineered PKSs that produce novel polyketides or 'unnatural' natural products (see PCT Pub. Nos. 99/61599, 00/024907, and 00/026349, each of which is incorporated herein by reference). Recent work has culminated in the generation of libraries of ~100 macrocyclic compounds, illustrating the potential to create libraries with significant complexity and diversity (see PCT Pub. Nos. 00/063361 and 00/024907, each of which is incorporated herein by reference).

The ability to manipulate predictably the catalytic activities of these multifunctional enzymes represents significant technological achievements in protein engineering. However, one of the current challenges to the construction of very large compound libraries (>1000 compounds) is the decline in production levels associated with many genetically modified PKSs, particularly those in which multiple domains have been modified (PCT Pub. Nos. 00/063361 and 00/024907, supra). While it is desirable to use PKS structure-activity knowledge to help guide more optimal engineering of PKSs, due to the complexity and size of these enzymes, the current understanding is relatively limited, and progress has been slow. It is therefore important to develop complementary approaches that do not rely on a detailed understanding of the enzymatic architecture to improve combinatorial biosynthesis technologies.

One possibility leverages the significant resources that are generally devoted over the course of many years towards establishing commercial processes to produce natural product pharmaceuticals. Almost inevitably, extensive strain improvement and process development programs are undertaken to increase the yield of compound from the natural producing organism, often achieving greater than 100-fold increases in titers. A number of microorganisms have been optimized through random mutagenesis for bulk production of highly valuable compounds, including penicillins, macrolide antibiotics, and lovastatins. Although this conventional approach to strain improvement could be applied to strains carrying engineered PKSs, it is a labor-intensive process, especially given the potentially large numbers of mutant strains that could be generated by combinatorial biosynthesis. However, if overproduction capabilities of existing industrial strains could be applied to increase titers of polyketides derived from engineered PKSs, it would present an attractive and economical solution. Not only would overproduction increase the accessibility of compounds produced at levels currently too low for screening, but also the size of libraries created could be enlarged, because more modifications could be introduced into a PKS before productions levels became too low. The broad applicability of such strains, however, depends on what factors are responsible for overproduction, and whether production from a recombinant PKS would be increased in an overproduction background.

The present invention meets the need for a generic host cell capable of producing a polyketide at levels significantly higher than in other host cells.

SUMMARY OF THE INVENTION

In a first embodiment, the present invention provides a method for producing a first polyketide, said method comprising expressing polyketide synthase (PKS) genes encoding a PKS that produces the first polyketide in a cell that has been optimized for the production of a second polyketide.

In one aspect, this method involves the production of a first polyketide that is a derivative of the second polyketide and altering the PKS genes in the overproducing cell such that those genes express a PKS that produces the first polyketide.

In another aspect, this method involves the introduction of genes that express a PKS that produces the first polyketide into the overproducing cell. In a preferred mode, the genes that express the PKS that produces the second polyketide are deleted or otherwise rendered inactive before or after introduction of the genes that encode the first PKS.

In a preferred embodiment of this method, the overproducing cell produces the second polyketide at a level greater than 1 g/L, preferably greater than 2.5 g/L, more preferably greater than 5 g/L, and most preferably greater than 10 g/L. In a preferred embodiment of this method, the overproducing cell produces the first polyketide at a level greater than 10 mg/L, preferably greater than 25 mg/L, more preferably greater than 50 mg/L, and most preferably greater than 100 mg/L.

In another embodiment, the present invention provides a generic overproducing host cell from which the genes encoding the second polyketide have been deleted and in which the genes encoding the PKS that produces the first polyketide can be readily introduced and expressed.

In one aspect, this generic overproducing host cell is derived from a *Saccharopolyspora erythraea* host cell that produces erythromycins at a level exceeding 2.5 g/L and is modified either by deletion of all or substantially all of the eryA genes or by mutational inactivation of the ketosynthase (KS) domain of module 1 of the DEBS PKS.

In another embodiment, the present invention provides a generic overproducing host cell that has been modified to express the PKS that produces the first polyketide. In a preferred embodiment, the host cell contains an attachment site for the integrating phage phiC31 that facilitates transformation of the strain. In one embodiment the host cell has been modified by genetic alteration to include such an attachment site.

In one aspect, this generic overproducing host cell is derived from a *Saccharopolyspora erythraea* host cell that produces erythromycins at a level exceeding 2.5 g/L and is modified either by alteration of the eryA genes to encode a PKS that produces 10,11-anhydro-6-deoxyerythronolide B or by mutational inactivation of the ketosynthase (KS) domain of module 1 of the DEBS PKS.

These and other embodiments, modes, and aspects of the invention are described in more detail in the following description, the examples, and claims set forth below.

DETAILED DESCRIPTION OF THE INVENTION

In a first embodiment, the present invention provides a method for producing a first polyketide, said method comprising expressing polyketide synthase (PKS) genes encoding a PKS that produces the first polyketide in a cell that has been optimized for the production of a second polyketide. In a preferred embodiment of this method, the overproducing cell produces the second polyketide at a level greater than 1 g/L, preferably greater than 2.5 g/L, more preferably greater than 5 g/L, and most preferably greater than 10 g/L. In a preferred embodiment of this method, the overproducing cell produces the first polyketide at a level greater than 10 mg/L, preferably greater than 25 mg/L, more preferably greater than 50 mg/L, and most preferably greater than 100 mg/L.

Figure 1:
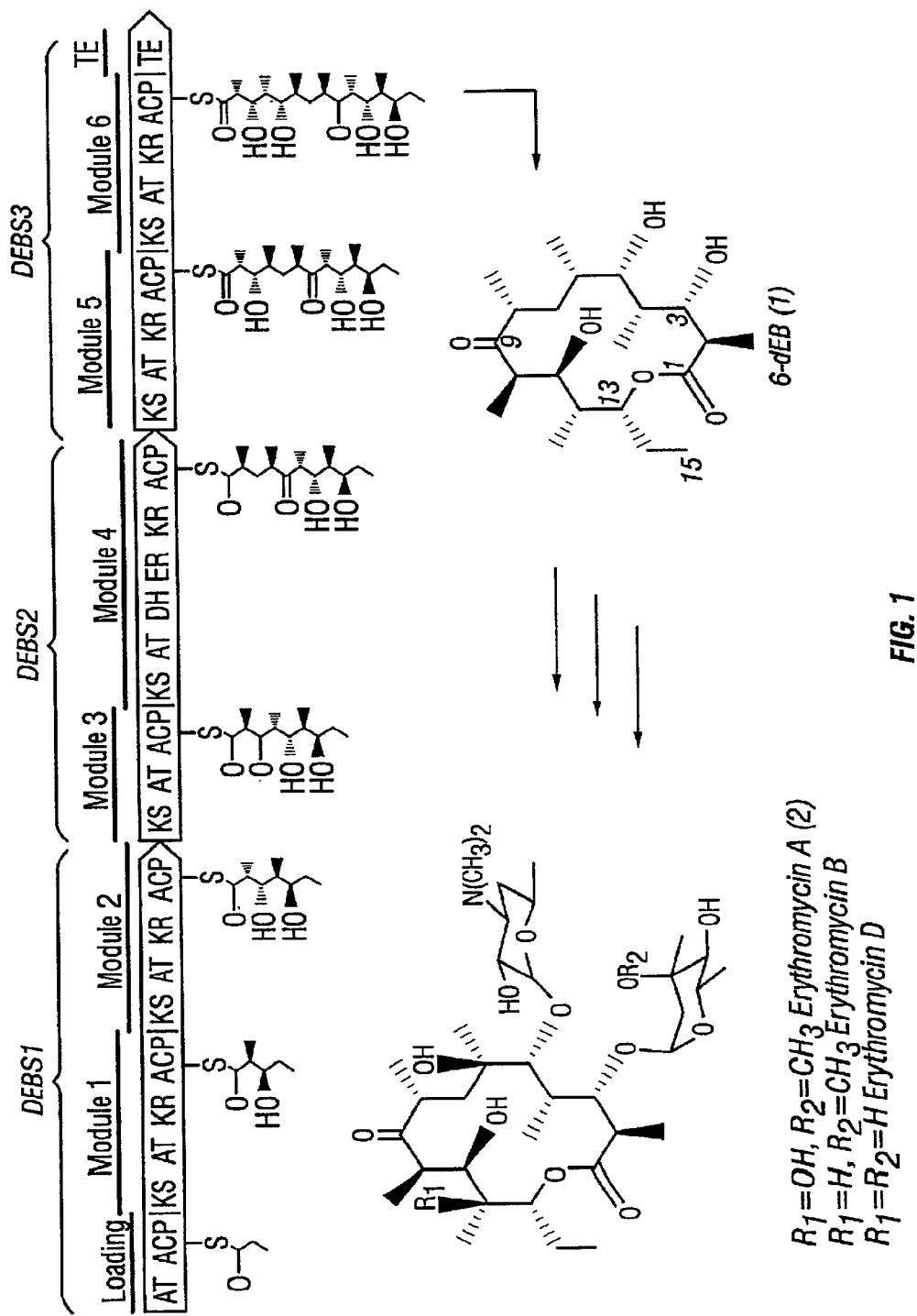
FIG. 1 shows key steps in erythromycin biosynthesis, including the modular organization of the three proteins (DEBS1, DEBS2, and DEBS3) that comprise DEBS, the intermediates formed at each step in the synthesis of 6-deoxyerythronolide B (6-dEB), and the structures of the erythromycins resulting from modification of 6-dEB (erythromycin C is not shown).

Because of the value of polyketides in medicine and agriculture, and because of the typically low amounts in which polyketides are produced in the cells in which they are found in nature, significant efforts have been made to increase polyketide production in cells. Thus, there are a number of "overproducing" cells that make polyketides. As but one example, the erythiomycins and semi-synthetic derivatives have important pharmaceutical application as anti-infective agents. DEBS, which synthesizes the macrolactone core of erythromycin, 6-deoxyerythronolide B (6-dEB, compound 1 in FIG. 1), belongs to the modular class of PKSs—so-called because the enzymatic domains required for synthesis are organized into modular repeats of catalytic domains (FIG. 1). *Saccharopolyspora erythraea* NRRL2338, the organism from which DEBS was originally cloned, typically produces between 100–200 mg/L of erythromycin A in standard laboratory fermentations. Heterologous expression of DEBS in either *Streptomyces coelicolor* or *S. lividans*, in which the hydroxylation and glycosylation pathways do not exist, yields approximately 50–100 mg/L of 6-dEB (1) under optimal conditions, which is similar to the amount of 1 generated by NRRL2338 (see U.S. Pat. No. 5,672,491, incorporated herein by reference). In contrast, many industrially optimized strains of *S. erythraea* produce >10 g/L of erythromycin.

The biochemical reasons for such overproduction are, however, unknown. One reason could be that, relative to a normal producer, the overproducer cell has one or more mutations in the genes coding for the expression of the PKS. Another reason could be that the overproducer cell simply produces more of the precursor compounds used in polyketide biosynthesis. If the reason for overproduction resides in the PKS genes, then an overproducer of a first polyketide would not likely be an overproducer of a second polyketide.

To illustrate the benefits of the present invention, an overproducing strain of *Saccharopolyspora erythraea* designated K1 capable of producing at least 7 g/L of erythromycin in bioreactor fermentations was employed. As noted above, surprisingly little has been reported about the determinants of overproduction in industrial microorganisms. Improvements in yield could result from mutations in biosynthetic enzymes that increase flux, up-regulation of corresponding gene expression, or higher intracellular pools of substrate (acyl-CoA thioesters in the case of polyketides). For an *S. erythraea* erythromycin overproducer, it is unlikely that a large increase in titer could be attributed solely to overexpression of DEBS, leaving a combination of the latter two as the most probable reason for high production levels in the *Saccharopolyspora erythraea* overproducer. To demonstrate that the overproducing strain did not possess a kinetically improved PKS, the PKS genes were cloned and expressed in *Streptomyces lividans* and *Streptomyces coelicolor* and production levels compared to the DEBS originally isolated from a wild-type *S. erythraea* strain. The results suggested that mutations in the PKS are not the likely cause of overproduction and that expression of PKSs from other organisms in this strain would lead to higher titers compared to parent strains.

To examine whether some or all of the improved production characteristics of the industrial *Saccharopolyspora erythraea* host were wholly or in part due to the activity of the PKS, the PKS was compared to DEBS from the NRRL2338 strain. Again, because this industrial strain was generated from many rounds of mutagenesis, it is possible that mutations had been introduced in the DEBS genes that resulted in higher biosynthetic throughput. If so, this could enable one to increase titers of erythromycin and related macrolides produced in heterologous hosts, such those previously made with DEBS in *Streptomyces coelicolor* or *S. lividans*, by employing the mutant PKS genes. Although the entire set of DEBS genes from the overproduction strain could be sequenced to identify potential mutations, the size of the gene cluster (>30 kb) makes this approach laborious. Instead, the three genes encoding DEBS, eryAI-III, were cloned from the overproducing strain and, using conserved restriction sites, placed in the same Streptomyces expression vector used for heterologous expression of DEBS obtained from *S. erythraea* NRRL2338. The resulting plasmid, pKOS108-04, is identical to pKAO127'kan' (which contains wild-type DEBS) except for the source of the eryAI-III genes. In each case, expression of the genes is controlled by the act I promoter and act II-4 regulatory proteins on the expression plasmid (see U.S. Pat. No. 5,672,491, incorporated herein by reference). Both pKOS108-04 and pKAO127'kan' were used to transform *S. lividans* K4-114 and *S. coelicolor* CH999. Multiple transformants (2–4 each) were grown in parallel, and the production profiles of 6-dEB were determined. In both *S. lividans* and *S. coelicolor*, the DEBS genes from the two different *S. erythraea* strains yielded equivalent amounts of 6-dEB (~30–40 mg/L) under the culture conditions described in the examples below.

The inability to increase polyketide titers with the PKS from the overproduction host implies that DEBS from this strain is not catalytically different from that of wild-type DEBS, although it is possible that 6-dEB production levels are limited by the amount of precursors available in these strains. The outcome of this experiment highlights the potential benefit of an industrial strain as a host for overproduction rather than the use of its PKS in a heterologous host. Thus, one benefit of the present invention is realized when an overproduction strain for one polyketide is genetically altered to express the PKS genes for a different polyketide.

In one aspect, this method involves the production of a polyketide that is a derivative of a second polyketide and altering the PKS genes in the overproducing cell such that those genes express a PKS that produces the first polyketide. This aspect of the invention is illustrated by an erythromycin overproducing strain of *Saccharopolyspora erythraea* optimized for combinatorial biosynthesis. A mutant of DEBS was constructed in this host by a catalytic domain substitution that changes the structure of the corresponding polyketide. Compared to expression of the same mutant DEBS expressed in *Streptomyces lividans*, a non-optimized host, the amount of altered polyketide produced was dramatically higher.

A number of strategies for manipulating the biosynthesis of polyketides have been established using DEBS and other modular PKSs. These include inactivation, deletion, and substitution of domains and modules, construction of hybrid modules by protein fusions, and complementation between PKS subunits from different sources. These experiments have been performed either in *Streptomyces coelicolor, S. lividans*, or a relatively low yielding strain of *S. erythraea*. In accordance with the present invention, the titers of polyketides generated by PKS strategies used routinely to engineer DEBS in these strains can be substantially enhanced in an overproducing strain.

Figure 2:
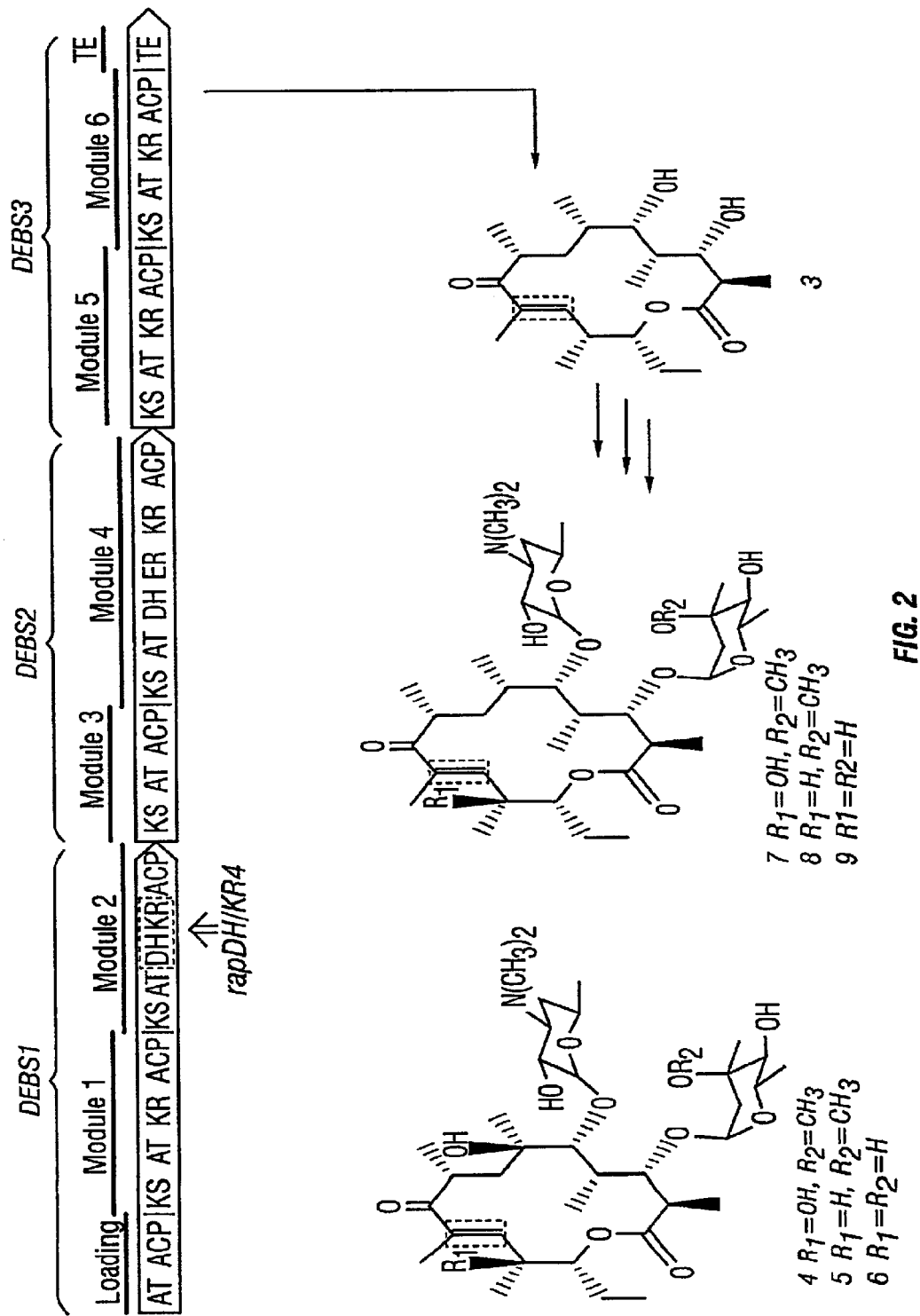
FIG. 2 shows the replacement in DEBS of the KR domain of module 2 with the KR and DH domains of module 4 of the rapamycin PKS and the products formed by the resulting recombinant PKS and action of polyketide modification enzymes in *Saccharopolyspora erythraea*.

To illustrate this benefit, a representative PKS domain substitution was constructed in an overproducing *Saccharopolyspora erythraea* strain. A replacement of the ketoreductase domain in extender module 2 of DEBS (eryKR2) with the DH and KR domains from extender module 4 of the rapamycin PKS (rapDH/KR4) was engineered in the chromosome of the overproducing host by homologous double recombination (FIG. 2). This particular mutation was chosen, because it was among the lowest producing functional single mutants that was generated in a systematic screening of domain substitutions and therefore rigorously tests the ability to improve low yielding PKSs. When engineered in a plasmid-based DEBS system and expressed in *Streptomyces lividans*, the resulting strain, *S. lividans* K4-114/pKOS11-64, produced approximately 0.3 mg/L of 3, the 10,11-anhydro analog of 6-dEB, as a result of the newly introduced DH activity (FIG. 2). See PCT Pub. Nos. 98/49315 and 00/02497, both of which are incorporated herein by reference.

*Saccharopolyspora erythraea* strain K39-10, which contains the substitution (Table 1), produced a mixture of erythromycin analogs in substantial amounts, all containing the expected 10,11-anhydro moiety, but differing in hydroxylation pattern (FIG. 2). The most abundant products were 10,11-anhydro erythromycin A (compound 4), B (compound 5), and D (compound 6), and 6-deoxy-10,11-anhydro erythromycin A (compound 7), B (compound 8), and D (compound 9). $^1$H-NMR spectroscopy and $^1$H-TOCSY correlations were used to confirm the structures of compounds 4, 5, 7, and 9 and determine the location of the hydroxyl groups in compounds 5 and 7. The ratio of these compounds produced can be media dependent. Whereas the B (12-deoxy) and D (4"-desmethyl) congeners of erythromycin A are often present in fermentation broth of *S. erythraea* strains, 6-deoxy compounds are usually not detected. EryF is the cytochrome P450 responsible for hydroxylation at the C-6 carbon of the polyketide aglycones. The presence of 6-deoxy compounds in K39-10 is consistent with previous observations in which in vitro hydroxylase activity of EryF was poor for substrates with a 10,11-double bond.

The total yield of erythromycins from either R5 or F1 fermentation medium was approximately 50 mg/L. This corresponds to ~26 mg/L of the macrolactone product (compound 3) synthesized by the engineered PKS. Although the yield of polyketide was significantly reduced compared to the amount of erythromycin produced by the parent strain, it constitutes nearly a 100-fold increase in titer compared to production of compound 3 in *Streptomyces lividans*. This relative increase matches the relative increase in 6-dEB production from unmodified DEBS in the two different hosts and demonstrates that most or all of the overproduction benefit is translated to the mutant PKS.

Two important discoveries emerged from these experiments that demonstrate that the use of high polyketide-producing strains is a general approach to the construction of large combinatorial libraries of polyketides. The first is that production levels from mutant PKSs can be significantly increased when expressed in overproducing backgrounds. This has been shown in an example with a domain substitution yielding relatively low amounts of compound compared to many other single modifications that have been made. Therefore, it is likely that such yield increases will be universally observed, including those involving PKS enzymes with multiple modifications relative to wild-type. With efficient genetic tools for this strain, it is relatively convenient to move existing macrolide libraries into *S. erythraea*, making the titers of compounds suitable for screening and expanding the number of compounds available.

Also, these experiments show that the causes of overproduction in this strain of *Saccharopolyspora erythraea* appear to lie within the background of the host and not from mutations in the PKS genes. This means that modules or domains from heterologous PKSs will also generate higher titers in the overproduction host. This is important, because functional units for PKS manipulation are available from a number of PKSs cloned from different organisms. Furthermore, it suggests that complete pathways of low producing PKSs, such as that for the antitumor polyketide epothilone, can be improved by heterologous expression, assuming sufficient substrate is available in the strain, and thereby circumventing the need for traditional strain improvement.

Thus, polyketide overproducing strains can be used to generate polyketides derivatives from engineered PKSs in good quantity. As shown herein, the use of an industrial erythromycin producing strain leads to production of an erythromycin derivative in quantity sufficient for biological assays from small scale production cultures (<1 L) and, with modest scale-up (100–1000 L), enough material for lead optimization by chemical modification. The present invention thus provides a simple and empirical method to achieve 'across-the-board' increases in titers from polyketide libraries prepared by combinatorial biosynthesis strategies, which translates into the ability to generate larger compound libraries in good yield. Furthermore, because the identification and cloning of polyketide gene clusters can be accomplished in relatively little time, it is now possible to shorten significantly process development time and effort of lead polyketides by heterologous expression in an overproducing host. Furthermore, it is possible to rescue declines in polyketide titers from engineered PKSs by using hosts optimized for very high production levels.

The methods of the invention can involve not only the alteration of existing PKS genes in the overproducer cell but also the introduction of new PKS genes into the overproducing cell. A large number of modular PKS genes have been cloned and are available for use in accordance with the methods of the invention. The polyketides produced by PKS enzymes are often further modified by polyketide modification enzymes, called tailoring enzymes, that hydroxylate, epoxidate, methylate, and glycosylate the polyketide product of the PKS. In accordance with the methods of the invention, these genes can also be introduced into the overproducer host cell to prepare a modified polyketide of interest. The following Table lists references describing illustrative PKS genes and corresponding enzymes that can be utilized in accordance with the invention. Also presented are various references describing polyketide tailoring and modification enzymes and corresponding genes that can be employed to make the recombinant DNA compounds of the present invention.

PKS and Polyketide Tailoring Enzyme Genes
Avermectin
U.S. Pat. No. 5,252,474; U.S. Pat. No. 4,703,009; and EP Pub. No. 118,367 to Merck.
MacNeil et al., 1993, *Industrial Microorganisms: Basic and Applied Molecular Genetics*, Baltz, Hegeman, & Skatrud, eds. (ASM), pp. 245–256, A Comparison of the Genes Encoding the Polyketide Synthases for Avermectin, Erythromycin, and Nemadectin.
MacNeil et al., 1992, Gene 115: 119–125, Complex Organization of the *Streptomyces avermitilis* genes encoding the avermectin polyketide synthase.
Ikeda and Omura, 1997, *Chem. Res.* 97: 2599–2609, Avermectin biosynthesis.
Candicidin (FR008)
Hu et al., 1994, *Mol. Microbiol.* 14: 163–172.
Epothilone
PCT Pub. No. 99/66028 to Novartis.
PCT Pub. No. 00/031247 to Kosan.
Erythromycin
PCT Pub. No. 93/13663; U.S. Pat. No. 6,004,787; and U.S. Pat. No. 5,824,513 to Abbott.
Donadio et al., 1991, *Science* 252:675–9.
Cortes et al., Nov. 8, 1990, *Nature* 348:176–8, An unusually large multifunctional polypeptide in the erythromycin producing polyketide synthase of *Saccharopolyspora erythraea*.

Glycosylation Enzymes
PCT Pub. No. 97/23630 and U.S. Pat. No. 5,998,194 to Abbott.
FK-506
Motamedi et al., 1998, The biosynthetic gene cluster for the macrolactone ring of the immunosuppressant FK-506, *Eur. J biochem.* 256: 528–534.
Motamedi et al., 1997, Structural organization of a multifunctional polyketide synthase involved in the biosynthesis of the macrolide immunosuppressant FK-506, *Eur. J Biochem.* 244: 74–80.
Methyltransferase
U.S. Pat. No. 5,264,355 and U.S. Pat. No. 5,622,866 to Merck.
Motamedi et al., 1996, Characterization of methyltransferase and hydroxylase genes involved in the biosynthesis of the immunosuppressants FK-506 and FK-520, *J. Bacteriol.* 178: 5243–5248.
FK-520
PCT Pub. No. 00/020601 to Kosan.
Nielsen et al., 1991, *Biochem.* 30:5789–96.
Lovastatin
U.S. Pat. No. 5,744,350 to Merck.
Nemadectin
MacNeil et al., 1993, supra.
Niddamycin
PCT Pub. No. 98/51695 to Abbott.
Kakavas et al., 1997, Identification and characterization of the niddamycin polyketide synthase genes from *Streptomyces caelestis*, *J. Bacteriol.* 179: 7515–7522.
Oleandomycin
Swan et al., 1994, Characterisation of a *Streptomyces antibioticus* gene encoding a type I polyketide synthase which has an unusual coding sequence, *Mol. Gen. Genet.* 242: 358–362.
PCT Pub. No. 00/026349 to Kosan.
Olano et al., 1998, Analysis of a *Streptomyces antibioticus* chromosomal region involved in oleandomycin biosynthesis, which encodes two glycosyltransferases responsible for glycosylation of the macrolactone ring, *Mol. Gen. Genet.* 259(3): 299–308.
PCT Pat. App. Pub. No. WO 99/05283 to Hoechst.
Picromycin
PCT Pub. No. 99/61599 to Kosan.
PCT Pub. No. 00/00620 to the University of Minnesota.
Xue et al., 1998, Hydroxylation of macrolactones YC-17 and narbomycin is mediated by the pikC-encoded cytochrome P450 in *Streptomyces venezuelae*, *Chemistry & Biology* 5(11): 661–667.
Xue et al., October 1998, A gene cluster for macrolide antibiotic biosynthesis in *Streptomyces venezuelae*: Architecture of metabolic diversity, *Proc. Natl. Acad. Sci. USA* 95: 12111 12116.
Platenolide
EP Pub. No. 791,656; and U.S. Pat. No. 5,945,320 to Lilly.
Rapamycin
Schwecke et al., August 1995, The biosynthetic gene cluster for the polyketide rapamycin, *Proc. Natl. Acad. Sci. USA* 92:7839–7843.
Aparicio et al., 1996, Organization of the biosynthetic gene cluster for rapamycin in *Streptomyces hygroscopicus*: analysis of the enzymatic domains in the modular polyketide synthase, *Gene* 169: 9–16.
Rifamycin
PCT Pub. No. WO 98/07868 to Novartis.
August et al., Feb. 13, 1998, Biosynthesis of the ansamycin antibiotic rifamycin: deductions from the molecular analysis of the rifbiosynthetic gene cluster of *Amycolatopsis mediterranei* S669, *Chemistry & Biology*, 5(2): 69–79.

Sorangium PKS

U.S. Pat. No. 6,090,601 to Kosan.

Soraphen

U.S. Pat. No. 5,716,849 to Novartis.

Schupp et al., 1995, *J. Bacteriology* 177: 3673–3679. A *Sorangium cellulosum* (Myxobacterium) Gene Cluster for the Biosynthesis of the Macrolide Antibiotic Soraphen A: Cloning, Characterization, and Homology to Polyketide Synthase Genes from Actinomycetes.

Spinocyn

PCT Pub. No. 99/46387 to DowElanco.

Spiramycin

U.S. Pat. No. 5,098,837 to Lilly.

Activator Gene

U.S. Pat. No. 5,514,544 to Lilly.

Tylosin

U.S. Pat. No. 5,876,991; U.S. Pat. No. 5,672,497; U.S. Pat. No. 5,149,638; EP Pub. No. 791,655; and EP Pub. No. 238,323 to Lilly.

Kuhstoss et al., 1996, *Gene* 183:231–6., Production of a novel polyketide through the construction of a hybrid polyketide synthase.

Tailoring enzymes

Merson-Davies and Cundliffe, 1994, *Mol. Microbiol.* 13: 349–355. Analysis of five tylosin biosynthetic genes from the tylBA region of the *Streptomyces fradiae* genome.

Any of the above genes, with or without the genes for polyketide modification, if any, can be employed in the overproducer host cells of the invention. Moreover, the host cells of the invention can be constructed by transformation with multiple vectors, each containing a portion of the desired PKS and modification enzyme gene cluster; see U.S. Pat. No. 6,033,883, incorporated herein by reference.

In a preferred mode, the endogenous PKS genes of the overproducer are deleted or otherwise rendered inactive before or after introduction of the genes that encode the PKS of interest. In one important aspect, the present invention provides a generic overproducing host cell from which the genes encoding the PKS that produces the "overproduced" polyketide have been deleted and into which the genes encoding the PKS of interest can be readily introduced and expressed. In one preferred embodiment, this generic overproducing host cell is derived from a *Saccharopolyspora erythraea* host cell that produces erythromycins at a level exceeding 2.5 g/L and is modified either by deletion of all or substantially all of the eryA genes or by mutational inactivation of the ketosynthase (KS) domain of module 1 of the DEBS PKS.

To illustrate this aspect of the invention, a genetic block on the polyketide synthase DEBS was introduced into an erythromycin overproducing strain of *Saccharopolyspora erythraea* resulting in non-production of 6-deoxyerythronolide. Expression of the oleAI gene of the oleandomycin PKS in this blocked strain was found to produce the 15-nor-erythromycin A. Exogenous addition of synthetic molecules to the cultures of this blocked mutant resulted in the production of novel, biologically active, C-13 derivatives of erythromycin analogs. This latter strategy, termed precursor directed biosynthesis, utilizes a biosynthetically blocked PKS mutant that can incorporate chemically derived priming units or intermediates downstream of the mutation in the PKS. Numerous C-13 derivatives of 6-dEB can be produced in *Streptomyces coelicolor* by introducing a mutation in the ketosynthase of module 1 (KS1) of DEBS, by incorporation of synthetic partial chains into the PKS (see PCT Pub. Nos. 99/03986 and 97/02358, both of which are incorporated herein by reference). However, it would be advantageous if this methodology could be practiced in an overproducing strain of *S. erythraea* so that not only could more polyketide be made but also fully glycosylated and hydroxylated compounds could be produced.

To accomplish this objective, plasmid pKOS40-57 was constructed as a delivery vector to introduce the active site Cys729->Ala mutation in the KS1 domain of DEBS1 module 1 as described in PCT Pub. Nos. 99/03986 and 97/02358, supra. The inactive KS1 domain prevents propagation of the starter unit and permits introduction of exogenous synthetic diketide thiol esters into the PKS (see PCT Pub. No. 00/044717, incorporated herein by reference). *Saccharopolyspora erythraea* K1 protoplasts were transformed with pKOS40-57, and eight transformants were obtained with no bioactivity against *Bacillus subtilis*. Genomic DNA was extracted from one of the transformants for PCR analysis to confirm the integration of pKOS40-57 at the appropriate location in the chromosome. Nonselective growth to allow plasmid eviction through a double crossover event was then conducted. Three out of five apramycin sensitive colonies were found to be the desired KS1 null (KS1°) mutants. One such KS1° null strain, designated K39-14, did not produce any detectable erythromycins or 6-dEB like products and showed no bioactivity when grown in R2YE medium. This K39-14 strain was used for the heterologous expression of the oleAI gene to complement the KS1 null mutation and for precursor-directed biosynthesis of novel erythromycin analogs.

Subunits from heterologous modular PKS can be functionally assembled to create hybrid polyketides. For example, both the DEBS3 and OleA3 (subunit 3 of the 8,8a-deoxyoleandolide PKS) subunits can fully complement the picromycin PikAIII and PikAIV subunits (see PCT Pub. No. 99/61599, incorporated herein by reference). The loading domain of wild-type DEBS from *Saccharopolyspora erythraea* has been shown to accept acetate to form low levels of 15-nor-erythromycin C. Similar results were observed when DEBS was expressed in Streptomyces coelicolor to form 15-nor-6dEB (1:5 of 6dEB) (see U.S. Pat. No. 5,672,491, incorporated herein by reference). The Ole PKS produces 8,8a-deoxyoleadolide, which differs from the product of DEBS, 6-dEB, by only one carbon in the priming unit. The subunits of the Ole PKS and DEBS contain significant structural differences: there is only ~45% identity between DEBS and the Ole PKS even though they are functionally similar.

Expression plasmid pKOS39-110, which carries the oleAI gene under the control of ermE* promoter, was available (see PCT Pub. No. 99/061599, incorporated herein by reference) and convenient to introduce the oleAI gene into strain K39-14 by integration into the chromosome using the ΦC31 attachment site. Transformation of *Saccharopolyspora erythraea* K39-14 with plasmid pKOS39-110 resulted in a strain that exhibited antibacterial activity of ~5 to 10 mg/L of 15-nor-erythromycin A with a minor compound 15-nor -erythromycin C. The mass spectrum and LC retention time were identical to known standards. The species of protonated molecular ion at m/z 706 is consistent with the proposed structure of 15-nor-erythromycin C. This result demonstrates that O1eAI can complement DEBS1 to some degree. The ability to express this heterologous PKS subunit in *S. erythraea* also demonstrates that heterologous PKS enzymes can be produced in the generic overproducer host cells of the invention.

Figure 3:
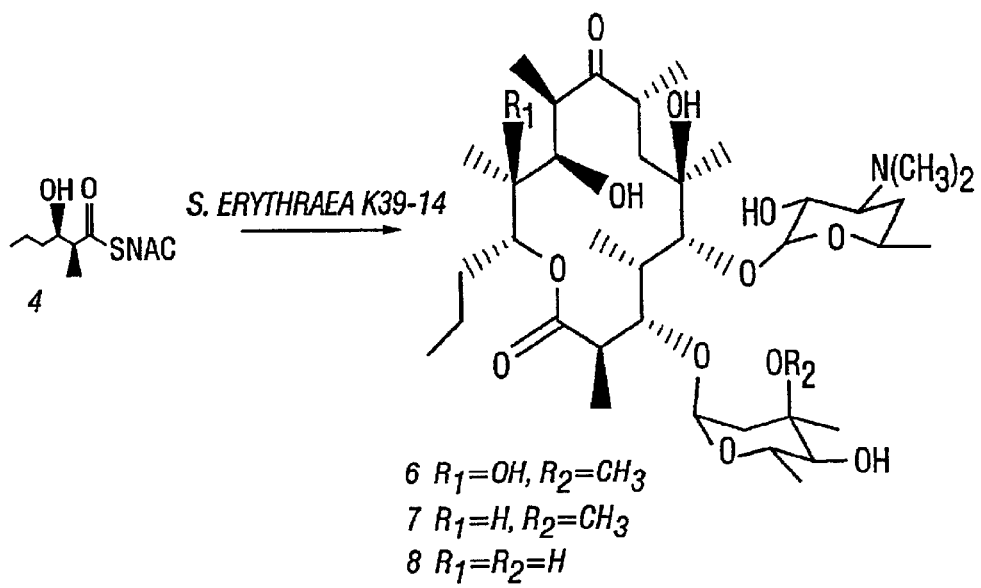
FIG. 3 illustrates production of erythromycin derivatives by precursor-directed biosynthesis, showing two diketides (compounds 4 and 5) and the products formed (compounds 6–11) upon providing them to a *Saccharopolyspora erythraea* host cell of the invention containing a KS1° mutation.
Figure 3:
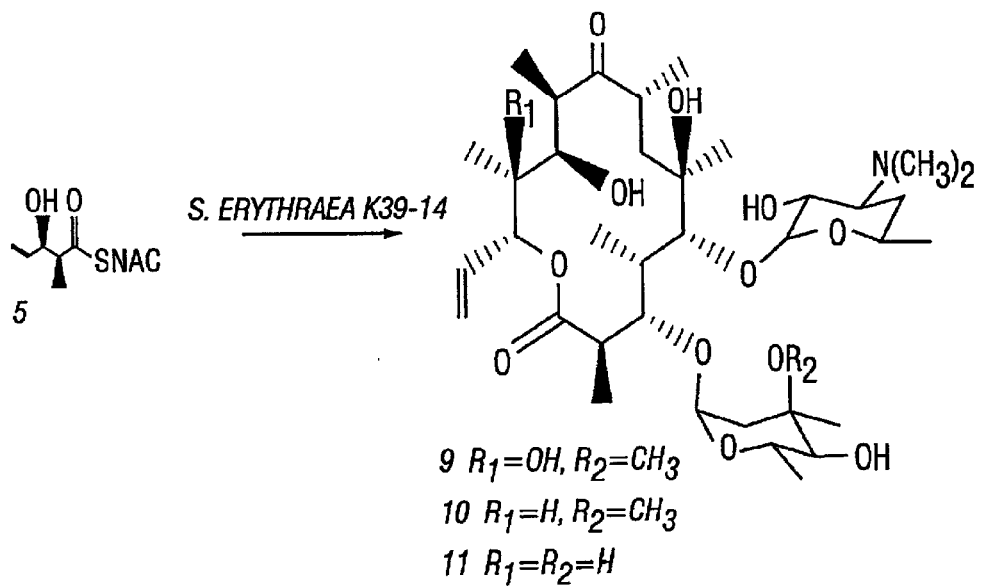

Precursor directed biosynthesis has been used to generate numerous C-13 derivatives of 6-dEB in *Streptomyces coeli-* color by introducing a mutation in the ketosynthase of module 1 (KS1) of DEBS and supplementing the fermentation with chemically synthesized N-acetyl cysteamine (NAC) thioesters of diketide precursors. To simplify the production of erythromycin analogs by precursor-directed biosynthesis and to process fully the polyketides produced into erythromycin A analogs, the KS1° mutation was introduced in the chromosome of a *Saccharopolyspora erythraea* overproducer to generate strain K39-14, which was fermented in F1 media (see Brunker et al., 1998, *Microbiol.* 144: 2441–2448, incorporated herein by reference) in the presence (0.25 g/L) of the propyl or vinyl NAC diketides 4 and 5 shown in FIG. 3. The strain produced between 10–20 mg/L of the corresponding 15-methyl erythromycin or 14,15-dehydro erythromycin derivatives (compounds 6–8 and 9–11, FIG. 2), respectively. Both the erythromycin analogs showed antibiotic activity against *Bacillus subtilis*. The structure of 15-methyl erythromycin A was confirmed by NMR.

While the amount of erythromycins is considerably lower than the potential capacity of the strain, possibly due to membrane transport barriers, these yields are sufficient for biological screening from small culture volumes. Given the possible array of synthetic diketides that can be chemically synthesized, it should be possible to generate and screen many more erythromycin derivatives in a convenient manner.

In accordance with the method of the invention, an overproducer strain of *Saccharopolyspora erythraea* has been used to produce several erythromycin compounds not naturally produced by the strain as major products. The OleAI complementation of the DEBS1 mutant containing a KS1 null mutation in the *S. erythraea* overproducer strain provides an example of a functional heterologous PKS composed of proteins derived from two different PKS enzyme complexes that produces a polyketide not made as a major product by the unmodified overproducer strain. The production of 10,11-anhydroerytliromycins in the *S. erythraea* overproducer strain provides an example of a functional heterologous PKS complex that contains a protein that comprises a module composed of enzymatic domains derived from two different PKS enzymes and produces polyketides not made by the unmodified overproducer strain. The production of polyketides by diketide feeding in the *S. erythraea* overproducer strain that contains a KS1 null mutation provides an example of a non-functional homologous PKS complex that can be used to produce a polyketide different from that produced by the wild-type PKS by providing a synthetic chemical starter for the PKS.

Thus, the present invention provides useful methods and host cells for producing many different polyketides in recombinant host cells. However, it is known that polyketide-producing host cells that have been optimized via mutagenesis to produce high titers of polyketides are refractory to transformation. Moreover, the low efficiency of transformation observed with such cells decreases significantly as the size of the vector used to transform the cell increases. For very large vectors, transformation often simply is not possible. Because PKS genes are typically very large (>30 kb), this low transformation efficiency presents a significant barrier in realizing the benefits of the present invention. There is some evidence and speculation that this transformation barrier may be due to restriction-modification systems in the host.

Conjugation-mediated transformation can overcome this barrier to some extent; this may be due to the lower susceptibility of the single-stranded DNA generated in conjugation to restriction-modification systems. However, even conjugation-mediated transformation may not be successful with very large vectors that integrate into the chromosome of the host cell by homologous recombination. This barrier may be due to the nature of the homologous recombination event, which may be slow relative to the cleavage of the delivered DNA by restriction-modification systems.

Vectors containing an attachment site (attp) from a phage, such as the vectors of the phiC31, pSAM, and pSLP vector systems, can integrate into the chromosome of a host cell by a mechanism mediated by the integrase enzyme of the phage. However, when such vectors were used in conjugation-mediated transformation with *Saccharopolyspora erythraea* host cells, as described above, very low transformation efficiencies were observed. The exconjugants were analyzed by DNA sequence analysis, and it was discovered that the vectors integrated randomly at sites that differed in sequence from previously identified preferred attachment site sequences utilized by the phage in other organisms (the attB sequence). This low transformation efficiency barrier was overcome by altering the chromosome of the host cell to contain an attB sequence. The resulting recombinant host cells could be transformed by conjugation with phiC31 attachment site sequence-containing vectors at relatively high transformation efficiencies, even with very large vectors containing entire PKS gene clusters.

Thus, in one embodiment, the present invention provides a recombinant host cell other than an *E. coli* or human host cell (see Thorpe et al., 1998, *Proc. Natl. Acad. Sci. USA* 95: 5505–5510, and Groth et al., 2000, *Proc. Natl. Acad. Sci. USA* 97: 5995–6000, both of which are incorporated herein by reference) that has been modified, relative to the cell from which it was derived, to contain one or more attB sites. A cell that has been modified to contain multiple attachment sites may be preferred for purposes of introducing multiple genes at different locations in the chromosome. In one embodiment, the cell is derived from a cell that has been optimized by mutagenesis to produce a polyketide at high levels. In another embodiment, the cell is a *Saccharopolyspora erythraea* host cell, such as NRRL2338 or a cell that produces erythromycins at greater than 2.5 g/L.

In another embodiment, the present invention provides a method for obtaining a transformant of a cell that has been modified to contain a phiC31 attachment site, which comprises conjugating said cell with a cell that contains a vector that comprises the complementary attachment site (attB is complementary to attP and vice versa) in the presence of an integrase (which may be the phiC31 integrase, and the gene therefore can be in the vector or in the host cell and can be under the control of a heterologous promoter). While attP is typically employed on the vector and attB on the chromosome, one may also place attP in the chromosome and attB on the vector in accordance with the methods of the invention. In another embodiment, the present invention provides the cells produced by such method. In a preferred embodiment, the cells produced by such method produce a polyketide that is not produced by the cells prior to said conjugating step.

The following examples are given for the purpose of illustrating the present invention and shall not be construed as being a limitation on the scope of the invention or claims.

EXAMPLE 1

Strains, Culture Conditions, and DNA Manipulation

DNA manipulations were performed in *Escherichia coli* XL1-Blue (Stratagene). The *Saccharopolyspora erythraea* overproduction strain produced erythromycins at up to 7 g/L (strain K1). Transformation of this strain was performed according to standard Streptomyces protoplast methods except TSB media was used in place of YEME. Transformants were selected with thiostrepton (50 μg/mL) or apramycin (100 μg/mL) overlay on R2YE or R5 regeneration plates.

EXAMPLE 2

Construction of a *Saccharopolyspora erythraea* KS1 Null Mutant Strain

Plasmid pKOS40-57 was constructed by introducing a 4.0 kb NdeI-EcoRV fragment containing a DEBS KS1 null mutation (specific replacement the active-site cysteine of DEBS KS1 domain with alanine; see Kao et al., 1996, *Biochemistry* 35: 12363–12368, incorporated herein by reference) into a suicide vector (a pUC18 derivative containing apramycin resistance conferring gene) as the delivery vector. Plasmid pKOS40-57 was transformed into *Saccharopolyspora erythraea* K1. Apramycin-resistant strains (K1-1) were grown in TSB medium containing apramycin (100 μg/ml) to confirm resistance, and integration was confirmed by PCR analysis of chromosomal DNA. For resolution of a double-crossover, transformants were passaged twice in TSB medium without apramycin. Protoplasts were regenerated on R2YE plates. Individual colonies arising on the regeneration plates were then screened for sensitivity to apramycin. A colony containing the desired mutation was demonstrated not to produce erythromycin and named *S. erythraea* K39-14. As described above, the K39-14 strain produced 15-nor-erythromycins when transformed with plasmid pKOS39-110 encoding the oleAI gene and produced 15-methyl-erythromycins when provided the propyl NAC diketide (compound 4 in FIG. 3).

EXAMPLE 3

Production and Analysis of Erythromycin Derivatives

*Saccharopolyspora erythraea* strains described herein were grown in 25 mL of R2YE for 5 days at 30° C. The cultures were analyzed by HPLC/MS for the erythromycin derivatives. Structure determination was based primarily on the agreement between the structure predicted for the engineered strains and the mass spectrum and HPLC profile. An *S. erythraea* wild-type strain was used as the reference for the mass spectrum and HPLC. Further structural validation by NMR spectroscopy on 15-methylerythromycin A was also performed, as described in Example 4. Biological activity was assessed by the agar plate diffusion assay with *Bacillus subtilis* as an indicator strain and incubated overnight at 37° C. to visualize zones of inhibition.

EXAMPLE 4

Characterization of 15-methylerythromycin A

*Saccharopolyspora erythraea* strain K39-114 was fermented as described in Example 3 in the presence of 0.25 g/L of the propyl NAC diketide (compound 4 in FIG. 3), which was provided to the culture 24 hours after fermentation began. 15-methylerythromycin A, extracted from fermentation, was further purified for characterization by column chromatography using 1:1 toluene/acetone to give a white solid. $^1$H and $^{13}$C spectra were recorded in CDCl$_3$ solution at 400 MHz (Bruker DRX). Thin layer chromatography was performed on pre-coated glass with silica gel 60 and the spots were visualized by vanillin stain followed by heating. NMR assignment: $^1$H NMR (400 MHz, CDCl$_3$) δ5.14 (dd, 1H, J=2.0, 8.8), 4.91 (d, 1H, J=4.8), 4.44 (d, 1H, J=7.2), 4.05–3.98 (m, 2H), 3.84 (br s, 1H), 3.60 (d, 1H, J=7.6), 3.54–3.47 (m, 1H), 3.34 (s, 3H), 3.25 (dd, 1H, J=7.2, 10.4,), 3.12 (br q, 1H, J=7.0), 3.04 (d, 1H, J=9.6), 2.90 (dq, 1H, J=7.2, 9.1), 2.77–2.67 (m, 1H), 2.52 (ddd, 1H, J=4.4, 9.6, 12.4), 2.43–2.37 (m, 1H), 2.34 (s, 6H), 2.05–1.90 (m, 2H), 1.90–1.80 (m, 2H), 1.79–1.55 (m, 3H), 1.50 (s, 3H), 1.36–1.09 (m, 27H), 0.94 (t, 3H, J=7.2). $^{13}$C NMR (100 MHz, CDCl$_3$) δ221.2, 174.6, 102.2, 95.4, 82.5, 79.0, 77.0, 76.3, 76.0, 74.1, 73.5, 71.6, 69.9, 68.0, 64.6, 64.5, 48.5, 44.2, 43.9, 39.2, 38.5, 37.6, 36.8, 34.0, 29.2, 27.8, 26.1, 20.5, 20.4, 18.5, 17.7, 17.3, 15.2, 14.9, 13.0, 11.0,8.1.

EXAMPLE 5

Generic Production Host Lacking Native PKS Genes

Numerous yield-enhancing mutations of the *Saccharopolyspora erythraea* high producer exist in regions of the chromosome other than the PKS genes, and affect precursor pools, regulatory processes, nutrient utilization, and other factors. Such yield-enhancing mutations can be directly and rapidly exploited by using the strain as a generic host for overproduction of polyketides encoded by mutant and heterologous PKS genes. The main requirement is the ability to provide all the starting materials used by the PKS and ancillary enzymes to make a particular polyketide. Fortunately, modular PKSs all use one or more of a small group of simple carboxylic acids (e.g., acetate, propionate or butyrate and their 2-carboxy derivatives) to build the carbon framework, and di- or trideoxyhexoses made from 1-thymidinediphosphoglucose to form glycosides of the primary polyketide. All the other tailoring reactions involve common cofactors available in most bacterial cells. Therefore, *S. erythraea* can provide all or most of the starting materials; any specialized ones needed for a particular polyketide could be introduced by genetic engineering.

One can replace the DEBS genes from a *Saccharopolyspora erythraea* erythromycin overproducer with heterologous PKS genes from non-overproducing strains. Enhanced production of the metabolite made by the introduced PKS gene will verify that the host indeed contains factors for metabolite overproduction that can be exploited for production of other polyketides. Before introduction of heterologous genes into the *S. erythraea* overproducer strain, one can first delete the native DEBS genes. As described in more detail below, this was accomplished by a two-step homologous recombination procedure. Sequences (~1.5 kb) flanking the DEBS genes were amplified by PCR and cloned into a suicide vector with a selectable marker (for apramycin resistance). The strain was transformed with the plasmid and single crossovers selected by using the selectable marker. Colonies were propagated under no selection and screened for loss of apramycin resistance, indicative of a double crossover recombination. The genotype of the double crossover candidates was confirmed by analysis with PCR, by loss of erythromycin production, and by Southern-blot hybridization. One such verified strain was designated K97-71.

*S. erythraea* K97-71 contains a chromosomal deletion of the three eryA genes and insertion of the xylE gene from *Pseudomonas aeruginosa* in their place in the chromosome. To make this strain, plasmid pKOS97-49b was first constructed as follows. Two fragments flanking the eryA genes were PCR amplified from *S. erythraea* genomic DNA using the following primers (SphI, HindIII, BamH I, and EcoRI restriction sites are underlined):
eryAI left flank, forward:
   5'-TTTGCATGCGGCCACGCGCACGTCGTGACC (SEQ ID NO:1),
etyAI left flank, reverse:
   5'-TTAAGCTTCATATGTCCCCCTACTCGACGAC CAC (SEQ ID NO:2);
eryAIII right flank, forward:
   5'-TTTGGATCCGGCGGAGGGAATACATGACCA CGAC (SEQ ID NO:3),
eryAIII right flank, reverse:
   5'-TTTGAATTCCCGCTCGCTGAAGTCCAGGCT (SEQ ID NO:4).

The two fragments were then cloned into pSET152 (see Bierman et al., 1992, Plasmid cloning vectors for the conjugal transfer of DNA from *Escherichia coli* to Streptomyces spp., *Gene* 116: 43–49, incorporated herein by reference) using the underlined restriction sites and corresponding sites in pSET152. The resulting plasmid was named pKOS97-49a.

The xylE gene was PCR amplified and cloned into the NdeI and XbaI sites of pKOS-97-49a to make pKOS97-49b. This plasmid no longer contains the phiC31 integrase gene and attP locus from pSET152 and serves as a suicide vector for delivery by homologous recombination.

Protoplasts of the overproducer strain *S. erythraea* K1 were generated by the standard procedure (see Hopwood et al., 1985, Genetic Manipulation of Streptomyces: A Laboratory Manual. The John Innes Foundation, Norwich, UK, incorporated herein by reference), except that cells were grown in TSB media and harvested after 3 days of growth. Plasmid pKOS97-49b DNA was prepared from *E. coli* ET12567 to generate non-methylated DNA and used to transform the protoplasts using the standard procedure (Hopwood et al., supra), except PEG3350 (Sigma) was used. Plates were overlayed with 1 mg of apramycin to select for integration of the plasmid by homologous recombination. Apramycin resistant colonies were analyzed by Southern hybridization to confirm single crossovers at the expected location. One colony was selected for carrying out a double crossover as follows. The strain was grown on IT agar media (per liter, 5 g glucose, 5 g tryptone, 0.5 g betaine hydrochoride, 5 g corn starch, 1 g corn steep liquor (50%), 200 mg $MgSO_4.7H_2O$, 2 mg $ZnSO_4\_7H_2O$, 0.8 mg $CuSO_4\_5H_2O$, 0.2 mg $CoCl_2\_6H_2O$, 4 mg $FeSO_4\_7H_2O$, 80 mg $CaCl_2\_6H_2O$, 150 mg $KH_2PO_4$, 10 g NaCl, 20 g agar) non-selectively until well-sporulated. Spores were harvested, dilutions were plated on IT plates, and single colonies were screened for loss of apramycin resistance. A single apramycin sensitive colony was isolated which did not produce erythromycin. The double crossover was confirmed by Southern hybridization. This strain was designated *S. erythraea* K97-71.

Strain K97-71 is a generic overproduction host of the invention into which one can insert PKS genes for other, non-6-dEB, polyketides. Because it may be difficult to move an entire set of PKS genes at once due to their large size (30 kb or larger), the construction can be broken into a series of 2 to 3 double homologous recombination steps if necessary. The picromycin PKS genes serve as an illustrative example of this aspect of the invention. The picromycin PKS is related to DEBS, but produces a significantly different compound. The picromycin PKS synthesizes narbonolide, which is similar to 6-dEB except for the lack of a methyl group at carbon 10, a double bond between carbons 10 and 11, and a ketone at carbon 3. These result from differences in modules 2 and 6 of the picromycin PKS. The AT domain of module 2 of the PKS incorporates acetate instead of propionate, there is an additional dehydratase (DH) activity in module 2, and there is no ketoreductase (KR) domain in module 6. The architecture of the picromycin and DEBS PKSs are also similar, except that modules 5 and 6 of the former are divided into two ORFs. The amino acid sequence similarity between the two PKSs is ~40%. Together, these distinguishing features of the picromycin PKS make it an ideal choice to demonstrate that modular PKSs different from DEBS will overproduce polyketides when transferred to the erythromycin overproducing organism.

To introduce the heterologous PKS genes, one can use a plasmid containing the attP attachment site. Alternatively, one can use the double recombination procedure described above. Once the complete PKS has been introduced, the strain is analyzed for production of metabolites. Because the erythromycin deoxysugar biosynthetic genes and the glycosyltransferase genes will remain intact, it is possible that either the polyketide aglycone (i.e. narbonolide), the desosaminylated derivative (narbomycin), or both may be produced depending on the activity of the glycosyl transferase present in the ery gene cluster. Furthermore, either of the C-6 or C-12 hydroxylation reactions may take place. The total amount of polyketides produced is compared directly with levels of erythromycin A production in the parent strain under the same conditions to demonstrate overproduction.

Other PKS genes can be readily introduced into strain K97-71, including but not limited to the megalomicin PKS (see PCT patent application No. US00/27433, filed Oct. 4, 2000, incorporated herein by reference) and oleandolide PKS (see PCT Pub. No. 00/026349, incorporated herein by reference) genes. This host can also be used for production of polyketides only distantly related to erythromycin, such as FK506 and epothilone. This could also involve introduction of certain non-PKS genes to ensure production of unusual substrates for the PKS enzymes (e.g., 2-ethyl or 2-hydroxymalonate) or provide enzymes that modify the polyketide skeleton as it is being formed (e.g., dehydration or oxidation). Moreover, one can employ any of a variety of promoters, such as an act promoter, an ermE* promoter, an eryA promoter from an erythromycin overproducing strain, to drive expression of the heterologous PKS gene cluster.

EXAMPLE 6

Construction of an *S. erythraea* Strain that Contains a PhiC31 Attachment Site

*Saccharopolyspora erythraea* strains do not contain chromosomal DNA sequences corresponding exactly to the attachment site sequences of phiC31. Thus, conjugation efficiencies with phiC31-derived plasmids are not high with such strains, and the introduction of very large plasmids into such strains can be difficult, if not impossible. Consequently, the present invention provides a variety of polyketide producing strains, including but not limited to *S. erythraea* strains, that have been improved by the insertion of phiC31 attachment site sequences into the chromosomal DNA of the strain.

*S. erythraea* K24-1 contains a chromosomal deletion of the three eryA genes and insertion of the attB locus for the *Streptomyces* phage phiC31 from *Streptomyces lividans*, followed by the ermE* promoter in their place. To make this strain, plasmid pKOS134-04 was first constructed as follows. The phiC31 attB site was inserted between the Hind III and BamH I sites of pKOS97-49a using the following two annealed oligonucleotides: forward:
5'-AGCTTCGGGTGCCAGGGCGTGCCCTTGGGCTC CCCGGGCGCGTAA-CTAGTG (SEQ ID NO:5), and reverse:
5'-GATCCACTAGTTACGCGCCCGGGGAGCCCAAG GGCACGCCCTGG-CACCCGA (SEQ ID NO:6).
This plasmid was designated pKOS024-87. Plasmid pKOS0134-04 was made by inserting a ~300 bp NheI/BamHI fragment containing the ermE* promoter between the resulting SpeI and BamHI sites of pKOS024-87.

Plasmid pKOS134-04 was introduced into *S. erythraea* K97-71 via conjugation from *E. coli*, as described below. Screening for single and double crossovers by homologous recombination were performed as described above. A double crossover strain verified by Southern hybridization was obtained and designated *S. erythraea* K24-1.

*S. erythraea* strains K97-71 and K24-1 were prepared by harvesting spores from strains grown on 1–2 IT plates, filtering the spores through sterile cotton, and resuspending in 1 mL of 20% glycerol. Spore suspensions were stored at ~20° C. A 20 µL aliquot of the spore suspension was added to 5 mL of 2×YT and incubated at 30° C. with shaking. After 1 hour, the spores were collected by centrifugation (recipient cells). Donor cells were prepared by transforming *E. coli*/pUZ8002 with pSET152 or pKOS97-113 or pKOS97-69a and selecting for apramycin resistance only. Plasmid pKOS97-113 and pKOS97-69a are derivatives of pSET152 that contain ~30 kb inserts harboring the megAI-III genes and the eryAI-III genes, respectively.

Several colonies were picked from the primary transformation plate and used to inoculate 5 mL of LB with chloramphenicol (10 µ/mL), kanamycin (100 µg/mL), and apramycin (60 µg/mL). The cells were grown at 37° C. for 3–4 hours (OD600 of 0.4–0.6), collected by centrifugation, washed in 5 mL of LB, centrifuged, and resuspended in 100 µL of LB. Conjugal transfer between the donor and recipient cells was performed by resuspending the recipient cells in the 100 µL of donor suspension and incubating at 37° C. without shaking for 15–30 min. The cells were spread on R5 plates containing 50 µg/mL nalidixic acid and incubated at 34° C. for 16 hours. The plates were then overlayed with 3 mL of soft nutrient agar containing 1 mg nalidixic acid and 2 mg apramycin. Exconjugants were observed after 48 hours of further incubation.

The conjugation frequencies were approximately 5×10-5 for K24-1::pSET152, 3×10-7 for K97-71::pSET152, 1×10-6 for K24-1::pKOS97-113, and less than ×10-7 for K97-71::pKOS97-114.

Plasmid integration into the chromosome of K24-1::pSET152 and K97-71::pSET152 exconjugants was confirmed as follows. Genomic DNA was prepared from several exconjugants of each strain, digested with BamHI or EcoRI, religated, and used to transform *E. coli*. Apramycin was used to select for recircularized DNA containing the integrated pSET152 vector and the attB/attP junction sequence in the chromosome. Plasmid DNA was prepared from apramycin resistant colonies and the attBlattP junction was sequenced using a primer which annealed upstream of the attP site in pSET152. In four separate K24-1::pSET152 exconjugants analyzed, pSET152 had integrated into four different chromosomal locations, none of which showed any similarity to known attB sites in other Streptomyces spp. In seven K24-1::pSET152 exconjugants analyzed, pSET152 had integrated into the engineered phiC31 attB in every case.

These results show that integrase-phiC31 mediated integration of vectors is not site specific in *S. erythraea* spp. in the absence of an engineered attB site and occurs at relatively low frequency. Placement of an appropriate attB or attP site, such as the one illustrated in this example, in the chromosome significantly increases the conjugation frequency of phiC31-based vectors and results in site-specific integration.

The invention having now been described by way of written description and examples, those of skill in the art will recognize that the invention can be practiced in a variety of embodiments and that the foregoing description and examples are for purposes of illustration and not limitation of the following claims.

What is claimed is:

1. A method for producing a first polyketide, said method comprising expressing polyketide synthase (PKS) genes encoding a first PKS that produce the first polyketide in an overproducing cell that has been optimized for production of a second polyketide, wherein the overproducing cell produces the second polyketide at a level greater than 1 g/L of culture medium, and wherein the genes encoding the second PKS are deleted or otherwise rendered inactive.

2. A method for producing a first polyketide, said method comprising expressing polyketide synthase (PKS) genes encoding a first PKS that produce the first polyketide in an overproducing cell that has been optimized for production of a second polyketide, wherein the overproducing cell produces the second polyketide at a level greater than 10 g/L of culture medium, and wherein the genes encoding the second PKS are deleted or otherwise rendered inactive.

* * * * *